US009936905B2

(12) United States Patent
Larson et al.

(10) Patent No.: US 9,936,905 B2
(45) Date of Patent: Apr. 10, 2018

(54) SENSOR WITH OPTICAL INTERFACE

(71) Applicant: Medtronic MiniMed, Inc., Northridge, CA (US)

(72) Inventors: Eric Allan Larson, Simi Valley, CA (US); Voltaire Isaac Lebron, Camarillo, CA (US); Kevin Holz, Santa Cruz, CA (US); Jasson Rodriguez, Rosemead, CA (US); Ameya Kantak, Pleasanton, CA (US); Soren Aasmul, Holte (DK)

(73) Assignee: Medtronic MiniMed, Inc., Northridge, CA (US)

( * ) Notice: Subject to any disclaimer, the term of this patent is extended or adjusted under 35 U.S.C. 154(b) by 414 days.

(21) Appl. No.: 14/512,778

(22) Filed: Oct. 13, 2014

(65) Prior Publication Data
US 2015/0119662 A1  Apr. 30, 2015

Related U.S. Application Data

(60) Provisional application No. 61/895,783, filed on Oct. 25, 2013.

(51) Int. Cl.
*A61B 5/1455* (2006.01)
*A61B 5/145* (2006.01)
(Continued)

(52) U.S. Cl.
CPC ........ *A61B 5/14532* (2013.01); *A61B 5/0059* (2013.01); *A61B 5/1455* (2013.01);
(Continued)

(58) Field of Classification Search
CPC . A61B 5/14532; A61B 5/1455; A61B 5/1495; A61B 5/1459; A61B 5/14546
See application file for complete search history.

(56) References Cited

U.S. PATENT DOCUMENTS 6,584,335 B1 * 6/2003 Haar ................. A61B 5/14532
                                                600/322
2002/0141062 A1 * 10/2002 Christoffersen ..... G02B 5/1852
                                                359/566
(Continued)

FOREIGN PATENT DOCUMENTS

JP    2003-241026    8/2003
JP    2003-295001    10/2003
(Continued)

OTHER PUBLICATIONS

International Search Report and Written Opinion from PCT/US2014/062008 filed Oct. 23, 2014.
(Continued)

*Primary Examiner* — Eric Winakur
(74) *Attorney, Agent, or Firm* — Gates & Cooper LLP

(57) ABSTRACT

A device for detection or measurement of a carbohydrate analyte in fluid comprises:
an optical sensor comprising components of an assay for carbohydrate analyte, the readout of which is a detectable or measurable optical signal, and a light guide having a distal portion optically coupled to the assay components and a proximal portion; and
a reader for interrogating the optical sensor, the reader comprising an assay interrogating system including a lens; and
an interface portion forming part of at least one of the optical sensor and the reader, the interface portion being capable of removably constraining the proximal portion of the light guide and the lens of the assay interrogating system in an optically coupled arrangement.
The device may be combined with an insulin-infusion system.

36 Claims, 11 Drawing Sheets

(51) Int. Cl.
*A61B 5/1473* (2006.01)
*A61B 5/00* (2006.01)
*A61M 5/14* (2006.01)
*A61M 5/172* (2006.01)
*A61M 5/142* (2006.01)
*G02B 6/32* (2006.01)
*G02B 6/42* (2006.01)
*A61B 5/1459* (2006.01)

(52) U.S. Cl.
CPC .......... *A61B 5/1473* (2013.01); *A61B 5/4839* (2013.01); *A61B 5/742* (2013.01); *A61M 5/1413* (2013.01); *A61M 5/14248* (2013.01); *A61M 5/1723* (2013.01); *A61B 5/0071* (2013.01); *A61B 5/1459* (2013.01); *A61B 2560/0443* (2013.01); *A61B 2560/063* (2013.01); *A61B 2562/16* (2013.01); *A61M 2230/201* (2013.01); *G02B 6/32* (2013.01); *G02B 6/4292* (2013.01)

(56) References Cited

U.S. PATENT DOCUMENTS

| | | | | |
|---|---|---|---|---|
| 2004/0180391 A1* | 9/2004 | Gratzl | ................ | A61B 5/14528 435/14 |
| 2005/0182299 A1* | 8/2005 | D'Amelio | .......... | A61B 1/00096 600/175 |
| 2006/0078908 A1* | 4/2006 | Pitner | .............. | G01N 33/54366 435/6.12 |
| 2008/0188723 A1* | 8/2008 | Kristensen | ....... | G01N 33/54373 600/316 |
| 2009/0177067 A1* | 7/2009 | Sode | .................. | A61B 5/14532 600/347 |
| 2009/0221891 A1* | 9/2009 | Yu | ...................... | A61K 49/0004 600/365 |
| 2013/0060105 A1 | 3/2013 | Shah et al. | | |
| 2015/0351669 A1* | 12/2015 | Weber | ................ | A61B 5/14532 600/316 |

FOREIGN PATENT DOCUMENTS

| | | | |
|---|---|---|---|
| JP | 2006-343448 | 12/2006 | |
| WO | 2008/029403 | 3/2008 | |
| WO | 2013/033076 | 3/2013 | |
| WO | 2013/036493 | 3/2013 | |
| WO | WO 2013033076 A1 * | 3/2013 | ............. A61B 5/742 |

OTHER PUBLICATIONS

JP Office Action dated Jul. 4, 2017, Application No. 2016-525861, with English translation.

* cited by examiner

SENSOR WITH OPTICAL INTERFACE

CROSS REFERENCE TO RELATED APPLICATIONS

This application claims priority under Section 119(e) from U.S. Provisional Application Ser. No. 61/895,783, filed Oct. 25, 2013, the contents of which are incorporated herein by reference.

FIELD OF INVENTION

The present invention relates to devices for detection and measurement of carbohydrate analytes e.g. glucose. Further aspects of the invention relate to components of such devices; to systems including such devices including closed-loop insulin-infusion systems; and to methods of making and using such devices, components and systems.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or produce insufficient quantities of insulin, then insulin must be provided to the body from another source.

Traditionally, since insulin cannot be taken orally, insulin has been injected with a syringe. More recently, the use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. Physicians have recognized that continuous infusion provides greater control of a diabetic's condition, and are increasingly prescribing it for patients.

Infusion pump devices and systems are relatively well-known in the medical arts for use in delivering or dispensing a prescribed medication, such as insulin, to a patient. In one form, such devices comprise a relatively compact pump housing adapted to receive a syringe or reservoir carrying a prescribed medication for administration to the patient through infusion tubing and an associated catheter or infusion set. Programmable controls can operate the infusion pump continuously or at periodic intervals to obtain a closely controlled and accurate delivery of the medication over an extended period of time. Such infusion pumps are used to administer insulin and other medications.

There is a baseline insulin need for each body which, in diabetic individuals, may generally be maintained by administration of a basal amount of insulin to the patient on a continual, or continuous, basis using infusion pumps. However, when additional glucose (i.e., beyond the basal level) appears in a diabetic individual's body, such as, for example, when the individual consumes a meal, the amount and timing of the insulin to be administered must be determined so as to adequately account for the additional glucose while, at the same time, avoiding infusion of too much insulin. Typically, a bolus amount of insulin is administered to compensate for meals (i.e., meal bolus). It is common for diabetics to determine the amount of insulin that they may need to cover an anticipated meal based on carbohydrate content of the meal.

Over the years, a variety of glucose sensors have been developed for use in obtaining an indication of blood glucose levels in a diabetic patient. Such readings are useful in monitoring and/or adjusting a treatment regimen which typically includes the regular administration of insulin to the patient.

It has been observed that the concentration of analytes in subcutaneous or interstitial fluid correlates with the concentration of said analytes in the blood, and consequently there have been several reports of the use of glucose sensors which are sited in a subcutaneous location. Such sensors may pass through the skin or may be remotely interrogated. Sensors which pass through the skin may include a base component which remains attached to the user's body, and a removable reader component used to obtain a reading from the sensor.

Several types of technology are available, with two of the most common and developed being electrochemical sensing and optical sensing. These types of sensor may be combined in an orthogonally redundant system as described in WO2013/036943.

Small and flexible electrochemical sensors, for example those constructed in accordance with thin film mask techniques, can be used to obtain periodic readings over an extended period of time.

Mansouri and Schultz (Biotechnology 1984; 2: pp. 885-890), Meadows and Schultz (Anal. Chim. Acta. 1993 280: pp. 21-30) and U.S. Pat. No. 4,344,438 all describe devices for the in situ monitoring of low molecular weight compounds in the blood by optical means. These devices are designed to be inserted into a blood vessel or placed subcutaneously with optical fiber connections to an external light source and an external detector.

One form of optical sensing makes use of a proximity-based signal generating/modulating moiety pair (discussed in U.S. Pat. No. 6,232,120), which is typically an energy transfer donor-acceptor pair (comprising an energy donor moiety and an energy acceptor moiety). The energy donor moiety is photoluminescent (usually fluorescent).

In such methods, an energy transfer donor-acceptor pair is brought into contact with the sample (such as subcutaneous fluid) to be analyzed. The sample is then illuminated and the resultant emission detected. One moiety of the donor-acceptor pair is bound to a receptor carrier (for example a carbohydrate binding molecule), while the other moiety of the donor-acceptor pair (bound to a ligand carrier, for example a carbohydrate analog) and any analyte (for example carbohydrate) present compete for binding sites on the receptor carrier. Energy transfer occurs between the donors and the acceptors when they are brought together.

An example of such donor-acceptor energy transfer is fluorescence resonance energy transfer (Förster resonance energy transfer, FRET), which is non-radiative transfer of the excited-state energy from the initially excited donor (D) to an acceptor (A).

An important characteristic of FRET is that it occurs over distances comparable to the dimensions of biological macromolecules. The distance at which FRET is 50% efficient, called the Förster distance, is typically in the range of 20-60 Å. Förster distances ranging from 20 to 90 Å are convenient for competitive binding studies.

Energy transfer produces a detectable lifetime change (reduction) of the fluorescence of the energy donor moiety. Also, a proportion of the fluorescent signal emitted by the energy donor moiety is quenched.

The lifetime change is reduced or even eliminated by the competitive binding of the analyte. Thus, by measuring the apparent luminescence lifetime, for example, by phase-modulation fluorometry or time-resolved fluorometry (see Lakowicz, Principles of Fluorescence Spectroscopy, Plenum Press, 1983, Chapter 3), the amount of analyte in the sample can be determined. The intensity decay time and phase angles of the donor are expected to increase with increasing analyte concentration. Thus, the FRET mechanism permits interrogation of the equilibrium state optically by illuminating the assay and measuring either the lifetime of the excited state ("lifetime interrogation"), and/or the intensity of the emitted fluorescence from the donor fluorophore ("intensity interrogation"). The latter approach is preferred, as it exposes the assay to 25 times less light than with the lifetime interrogation.

The FRET mechanism offers several advantages. First, FRET fluorescence lifetime measurements are generally insensitive to the relative position of the sensor and the reader unit as long as they are within optical reach of each other, and are also insensitive to changes in the environment, which helps make the system virtually calibration free. Second, FRET is considered very sensitive if the appropriate donor-acceptor ratio and suitable donor-acceptor geometry are obtained. These principles have been used in glucose sensing by energy transfer. WO91/09312 describes a subcutaneous method and device that employs an affinity assay based on glucose (incorporating an energy transfer donor-acceptor pair) that is interrogated remotely by optical means. Commonly-assigned WO97/19188, WO00/02048, WO02/30275, WO03/006992, WO03/072172, WO05/059037, WO05/064318, WO05/110207, WO06/010604, WO06/061207, WO06/061208, WO07/065653, WO09/024521 and WO09/024522 each describe developments of such methods and devices.

The above-described optical sensor technology offers several advantages over other available technologies. Optical sensors perform well in both the dermis and the subcutaneous region, which allows the optical sensor to maintain functionality even as the sensor is partially explanted, providing the patient with a measurement until the patient is able to replace the sensor. Due to the non-consuming and stable nature of the assay, the measurement technique is insensitive to bio-fouling. As such, it offers the possibility of one single point calibration throughout the entire lifetime of the sensor. Furthermore, the assay typically contains a reference dye, which remains stable with changing glucose concentrations, but is affected by many non-glucose induced changes. Therefore, it serves as a sensor diagnostic tool for the optical sensor, indicating when the integrity of the membrane has been compromised or the optical connection is misaligned.

Electrochemical sensors as described above have been applied in a telemetered characteristic monitor system as described, e.g., in commonly-assigned U.S. Pat. No. 6,809,653.

A characteristic monitoring system of the type described above is of practical use only after it has been calibrated based on the unique characteristics of the individual user. Accordingly, the user is required to calibrate the sensor externally. More specifically, a diabetic patient is required to utilize a finger-stick blood glucose meter reading an average of two to four times per day for the duration that the characteristic monitor system is used. Each time, blood is drawn from the user's finger and analyzed by the blood glucose meter to provide a real-time blood sugar level for the user. The user then inputs this data into the glucose monitor as the user's current blood sugar level which is used to calibrate the glucose monitoring system.

Such external calibrations, however, are disadvantageous for various reasons. For example, blood glucose meters include inherent margins of error and only provide discrete readings at one point in time per use. Moreover, even if completely accurate, blood glucose meters are cumbersome to use (e.g., one should not operate an automobile and take a finger stick meter reading at the same time) and are also susceptible to improper use. Furthermore, there is a cost, not to mention pain and discomfort, associated with each application of the finger stick. Thus, finger stick replacement remains a goal for the next generation of glucose monitoring systems.

As sensor technology improves, there is greater desire to use the sensor values to control the infusion of insulin in a closed-loop system (i.e., an artificial pancreas system). Specifically, a closed-loop system for diabetes includes a glucose sensor and an insulin infusion pump attached to the patient, wherein the delivery of insulin is automatically administered by the controller of the infusion pump-rather than by the user/patient-based on the sensor's glucose value readings. The benefits of a closed-loop system are several-fold, including tighter glycemic control during the night when the majority of hypoglycemic events Occur.

An accurate and reliable sensor has long been identified as a necessity for closed-loop realization. Glucose sensor technology has been evolving in an effort to meet the accuracy required for finger stick replacement and the reliability needed for consistent closed-loop functionality.

The inventors have found that performance of optical sensors which include base and reader components is very sensitive to the alignment of optical components in these components.

SUMMARY OF INVENTION

In a first aspect, the invention provides a device for the detection or measurement of a carbohydrate analyte in fluid comprising:
an optical sensor comprising components of an assay for carbohydrate analyte, the readout of which is a detectable or measurable optical signal, and a light guide having a distal portion optically coupled to the assay components and a proximal portion; and
a reader for interrogating the optical sensor, the reader comprising an assay interrogating system including a lens; and
an interface portion forming part of at least one of the optical sensor and the reader, the interface portion being capable of removably constraining the proximal portion of the light guide and the lens of the assay interrogating system in an optically coupled arrangement.

Preferably, the device is suitable for use in vivo. In preferred embodiments, the proximal portion of the light guide is disposed externally to a body of a user and the distal portion of the light guide and the assay components are placed internally in the user's body.

Preferably, the proximal portion of the light guide includes a proximal end of the light guide.

Preferably, when the proximal portion of the light guide and the lens are constrained in the optically coupled arrangement, the proximal end of the light guide is within the optical axis tolerance and/or the focal plane tolerance of the lens. The optical axis tolerance and focal plane tolerance acceptable for good performance are dependent on the fiber diameter, lens parameters and light source intensity.

Typically, the lens optical axis is parallel to the light guide optical axis as measured at the proximal portion of the light guide. Optical simulations show that a deviation of 8° from parallel allows light transmission of approximately 90% of the maximum light transmission which occurs when the optical axes are parallel. Thus, a deviation of the angles of the optical axes of up to 8° from parallel is acceptable.

The focal plane tolerance is discussed herein in terms of axes x and y, parallel to the focal plane of the lens and centered on the optical axis of the lens. During use of preferred embodiments of the device, axis x is preferably generally parallel to the skin of the user, and axis y is preferably generally perpendicular to the skin of the user.

The optical axis tolerance is discussed herein in terms of axis z, normal to the focal plane of the lens and centered on the focal plane of the lens. During use of preferred embodiments of the device, axis z is preferably generally parallel to the skin of the user.

Axes x, y and z, and the focal plane, focal point and optical axis of the lens are indicated in FIGS. 7 and 8. The point where x, y and z are 0 corresponds to the intersection between the optical axis of the light guide and the proximal end of the light guide being exactly at the focal point of the lens i.e. optimal optical coupling.

Preferably, the relative position of the light guide and lens is constrained within a tolerance range of ±10 to 200 µm in each of the x, y and z directions.

More preferably, the relative position of the light guide and lens is constrained within a tolerance range of less than or equal to ±125 µm, preferably less than or equal to ±50 µm, in the x and y directions (that is, in preferred embodiments, the optical axis of the light guide is aligned so that it is displaced by a maximum of at most 50 µm in any transverse direction from the optical axis of the lens).

Preferably, the relative position of the light guide and lens is constrained within a tolerance range of less than or equal to ±125 µm, preferably less than or equal to ±70 µm, in the z direction (that is, in preferred embodiments, the position of the proximal portion of the light guide is constrained so that it is displaced by a maximum of at most 70 µm from the focal point along the optical axis of the lens). Experiments indicate however that a tolerance of 250 µm may be acceptable in the z direction.

Preferably, the device further comprises a detachable connection between the optical sensor and the reader, the detachable connection being capable of further constraining the proximal portion of the light guide and the lens of the assay interrogating system within the optically coupled arrangement. Thus, the interface portion may constrain the relative position of the light guide and lens in the x, y and z directions, but more preferably the interface portion constrains the relative position of the light guide and lens in the x and y directions, with the relative position in the z direction being constrained by a separate connection of the optical sensor and reader as discussed in more detail below.

Preferably, the interface portion is a light guide interface portion forming part of the reader as discussed in more detail below. Generally, it is preferred for cost reasons to include constructional features on the reader rather than the optical sensor where possible, as the optical sensor has a shorter useful lifetime.

However, some or all of the interface portion may form part of the optical sensor. Thus, the optical sensor may include a female portion (for example a collar around the light guide) capable of interacting with a male portion on the reader. For example, a collar around the light guide may interact with a protrusion on the reader. This has the potential advantage of protecting the light guide.

Components of Device
  Components of the device include some or all of:
  optical sensor
    base including connectors
    light guide
    assay compartment
    assay components
  reader
    light guide interface portion
    assay interrogating system
      lens
      light detector
      other optical components including beam splitters, filters and mirrors
      optical system housing
      lens-retaining insert
    transmitter and further components
    housing including connectors
  These components are discussed in more detail below.

Optical Sensor

In preferred embodiments, the optical sensor remains in position on/in the user's body over its lifetime which may for example be up to 7 days. The reader typically remains connected to the sensor throughout the sensor's lifetime.

Base

Preferably, the proximal portion of the optical sensor light guide (disposed externally to the user's body) is mounted to a base.

The base is preferably mounted in use to the user's skin e.g. using adhesive on its lower surface or overtaping. Taping arrangements used in the ENLITE™ sensor may be applied.

The base may be formed partially or completely of plastics.

Preferably, the optical sensor and reader include at least one connection arrangement for mechanical connection, so that the optical sensor and reader can be connected, detached and re-connected.

More preferably, the optical sensor is adapted to connect to the reader by means of several connection arrangements as explained below. It will be appreciated that where one component of a connection arrangement is described as being part of the optical sensor and another component as being part of the reader, the opposite is also possible. A separate connector component may also be used, for example the further locking component mentioned below. Connection arrangements used in the SOF™ sensor may be applied.

As part of such a connection arrangement, the optical sensor base preferably includes a projecting portion for engaging a bore of the reader. The projecting portion may include an engaging surface, e.g. one or more O-rings, to facilitate engagement. This may provide a general location for the proximal portion of the light guide, with its specific location being determined by the light guide interface portion discussed below. Preferably the projecting portion locates the proximal end of the light guide within the light guide interface portion of the reader.

As an additional or alternative part of such a connection arrangement, the optical sensor preferably includes connectors for detachable connection to complementary connectors of the reader. The connectors suitably form part of the base. The connectors of the optical sensor preferably include one or more fasteners or latches, preferably moveable latches, for example flexible clips (e.g. resiliently biased clips), which may interact with fixed connectors of the reader.

Preferably, the connectors control the relative position of the light guide and lens in the z direction.

As an additional or alternative part of such a connection arrangement, the optical sensor and reader may comprise an anti-rotation arrangement (e.g. a keying arrangement) to prevent relative rotation of the optical sensor and reader when mounted to one another. In a preferred embodiment, one or more lugs on the reader engage complementary recesses on the optical sensor base. The lugs/recesses may for example be above and below the projecting portion and/or to each side of the projecting portion.

Optionally, a further locking component (also referred to herein as a "clip") inhibits or prevents relative movement of the light guide and lens in the z direction, preferably by occupying space between the optical sensor and reader. The locking component is suitably a separate component and is typically of plastics.

Relative movement of the lens guide and lens is optionally limited further still by connection of the reader to the optical sensor's overtaping e.g. via hook and loop fastening, and/or by overtaping of the reader.

Preferably, the base at least initially includes an injector (also referred to herein as an "insertion device" or "serter") for positioning the distal end of the light guide in the user's body. This may be a needle which partially or fully encases the distal portion of the sensor e.g. a needle of C-shaped cross-section as disclosed in WO2013/036493. The insertion device is preferably designed to minimize trauma and maximize patient comfort and consistency of sensor delivery. Insertion devices used in the ENLITE™ sensor may be applied.

Optionally, the base includes components of an electrochemical sensor.

Light Guide

Preferably, the light guide comprises one or more optical fibers. Preferably, the outer diameter of the light guide (or alternatively of each optical fiber) is in the range of 50 to 600 µm, more preferably in the range of 200 to 300 µm (e.g. 235 to 275 µm). Optical fibers of a low diameter may not capture sufficient light to transmit a good optical signal, whereas optical fibers of a high diameter are potentially painful to the user.

Preferably, the angle between the longitudinal axes of the proximal and distal ends of the light guide is in the range of 0 to 90°. An angle approaching 90° is preferred for needle insertion and to keep the device height to a minimum (as this allows the distal portion of the light guide to be perpendicular to the user's skin while the proximal portion is parallel to the user's skin), but a high angle may cause light guide cladding to crack. An angle of 45° may be used. Preferably, the light guide is flexible.

Preferably, the proximal end of the light guide includes an end face which is preferably planar and is preferably perpendicular to a longitudinal axis of the light guide.

The light guide is preferably of plastics. It preferably has a cladding e.g. a cladding of thickness around 10 µm. The light guide should have very low or no absorption of water and other liquids.

The light guide should transmit light of the wavelengths used for excitation, assay signal and reference with little to no attenuation.

Assay Compartment

Preferably, the assay components are retained in one or more assay compartments. In preferred embodiments an assay compartment is defined by the distal part of the light guide and a material that permits diffusion of the analyte but not the assay components (e.g. an analyte-permeable membrane). Preferred materials are copolymers having hydrophobic units and hydrophilic units, the hydrophilic units each comprising an ester of polyethylene glycol and a diacid, as disclosed in WO05/1102007. Particularly preferred materials are 1000PEGT80PBT20 disclosed therein and 1000PEGT70PBT30.

Suitably, the assay compartment is at or close to the distal end of the light guide. The assay compartment may lie wholly or partly within a recess or through hole of the light guide. Examples of such designs include a laser-drilled hole, or a rectangular cavity in the side wall of the light guide.

Assay Components

Preferred assay components are discussed in WO2013/036943.

In preferred embodiments, the analyte is glucose.

The assay is preferably a competitive assay.

Preferably, the assay components include an analyte binding molecule labelled with one of a proximity based signal generating/modulating moiety pair; and an analyte analog capable of competing with the analyte for binding to the analyte binding molecule labelled with the other of the proximity based signal generating/modulating moiety pair. The assay may further include a reference fluorophore which serves, inter alia, as a sensor diagnostic tool.

Preferably, the assay components include a carbohydrate binding molecule and a carbohydrate analog, and energy donor and acceptor moieties (also referred to as "the FRET pair") which provide an optical signal. The energy acceptor moiety has an absorption spectrum overlapping the energy donor moiety's emission spectrum. More preferably, the energy acceptor moiety is non-fluorescent.

In preferred embodiments, the assay is a competitive glucose binding affinity assay that includes a glucose receptor (the carbohydrate binding molecule), a glucose analog, a first fluorophore (the energy donor moiety) labeled onto the glucose receptor, and an acceptor dye (the energy acceptor moiety) labeled onto the glucose analog.

A preferred carbohydrate binding molecule is labelled MBL (mannose binding lectin). Concanavalin A is another carbohydrate binding molecule of interest.

Preferred carbohydrate analogs are labelled macromolecules bearing carbohydrate or carbohydrate mimetic moieties. Examples include optionally derivatized labelled dextran e.g. 110 kDa dextran; labelled synthetic polymers bearing pendant carbohydrate or carbohydrate mimetic moieties; labelled proteins bearing pendant carbohydrate or carbohydrate mimetic moieties. Such carbohydrate analogs are disclosed for example in WO07/065653 and WO06/061208.

Preferred energy donor moieties are Alexa Fluor fluorophores, Texas Red, and Cy5. Alexa Fluor 594 (AF594) is particularly preferred. AF647, QSY 21, and AF750 are appropriate for use in conjunction with a laser diode source at 645 nm.

A preferred energy acceptor moiety is hexamethoxy crystalviolet-1 (HMCV1, a proprietary crystal violet derivative manufactured by Medtronic, Inc.), disclosed in WO05/059037. This is particularly suitable where the carbohydrate analog molecule is dextran.

A preferred reference fluorophore is Alexa Fluor 700 (AF700). The reference fluorophore is preferably labeled onto Human Serum Albumin (HSA) or another macromolecule which does not bind significantly to the carbohydrate binding molecule.

In preferred embodiments of the invention, it has been found that a degree of labeling (DOL) with AF594 of about 0.8-1 AF594/CRD and 5 HMCV1 molecules per dextran molecule gives optimal dose-response.

The assay components may also comprise a protective formulation for radiation sterilization.

Reader

The reader is also referred to as the "recording device" or "Glucose sensor transmitter or recorder" (GST/GSR).

The reader is used to interrogate the optical sensor, and can be removably physically and optically coupled thereto.

The reader preferably includes a housing, e.g. of plastics. The reader may be wearable on the body of the user, and may be sized so as to have a volume of no more than 15 cm$^3$ (e.g. about 11 cm$^3$) and a weight of about 10 g. Preferably, the reader has a life of 2 years or more. The reader may need to be charged periodically e.g. every 15 days.

The reader preferably includes components of connection arrangements for detachable connection to the optical sensor. This is discussed in more detail above. In preferred embodiments the reader includes: a bore for engaging a projection portion of the optical sensor; fixed connectors for connection to moveable connectors of the optical sensor; anti-rotation lugs for engaging recesses of the optical sensor. Some or all of these features are suitably formed as part of reader housing.

Assay Interrogating System

The reader includes an assay interrogating system which receives an optical signal from the optical sensor via the lens referred to above. The assay interrogating system is preferably an optoelectronic interrogating system. The assay interrogation system may operate via lifetime and/or intensity interrogation of the assay as discussed above.

The lens is preferably a focusing/converging lens e.g. a biconvex lens. The lens is preferably of plastics.

The assay interrogating system suitably includes one or more light detectors e.g. photodiodes. In use, an optical signal in the form of light reaches the proximal end of the light guide, and is focussed via the lens and then transmitted to the light detectors.

Preferably, the assay interrogating system includes an illumination source e.g. an LED or a red laser diode, with the latter enabling a substantial reduction in the size and volume of the reader. AF647, QSY 21, and AF750 may be used in conjunction with a laser diode source at 645 nm. Typically, the illumination source is used to interrogate the assay via the light guide.

The assay interrogating system may include filters for example in the form of a filter substrate having one or more coatings to effect, e.g., an excitation filter and/or one or more emission filters.

The assay interrogating system may include further components e.g. beam splitters and/or mirrors. Typically beam splitters are present, but mirrors may not be present.

Components of the assay interrogation system are preferably included in an optical system housing sub-unit of the reader, which is preferably mounted to the reader housing.

Components of the assay interrogation system are preferably electrically connected to a printed circuit board assembly (PCBA). The components of the assay interrogating system may be mounted to the PCBA via alignment pins and/or screws, or the components may be electrically connected to the PCBA via flex connectors.

As an alternative to separate optical components, the assay interrogating system may be manufactured as a wafer-scale stacked planar integrated optical system (SPIOS) and diced into smaller units. A Stacked Planar Integrated Optical System (SPIOS) may be created by fixing one multi-functional filter layer between two injection molded layers of optical components to forms a solid block, which is self-supporting.

Light Guide Interface Portion and Lens

The reader preferably includes a light guide interface portion (also referred to herein as an "interface portion") of the reader. This is suitably a block of tightly controlled dimensions containing a blind or through opening. The light guide interface portion of the reader is preferably mounted to the optical box e.g. via an interference fit.

Preferably, the light guide interface portion comprises a female part, e.g. a flared opening, adapted to receive the proximal portion of the light guide.

The term "flared opening" includes arrangements with a narrow portion proximal to the lens and a wider portion distal to the lens. The proximal portion of the flared opening preferably ends in a light guide alignment channel adapted to accommodate the proximal end of the light guide. Suitably, the alignment channel is a circular cross-section channel of diameter slightly larger (e.g. up to 50 μm larger, more preferably up to 30 μm larger) than the light guide. The flared opening guides the light guide proximal end face into its optical coupling position with the lens, without damaging its surface.

The flared opening preferably comprises one or more chamfers i.e. continuous curved and/or planar surfaces which are not interrupted by edges, projections or other abrupt discontinuities in shape.

The flared opening of the light guide interface portion of the reader is preferably partially or completely conical or frusto-conical in shape. The cone half angle (or effective half angle) is preferably in the range of 25 to 43° e.g. around 30°. A half angle which is too high may prevent the light guide from being guided into position correctly.

However, the opening need not be conical, so that the half angle may vary from the proximal to the distal portion of the flared opening, or around the flared opening. For example, an arrangement with two or more chamfers, e.g. a double chamfer arrangement, may be used, as shown in FIG. 10. In the light guide interface portion on the left, a double frusto-conical arrangement is shown with an outer half angle of 45° and an inner half angle of 20°. In the light guide interface portion on the right, a single frustoconical arrangement is shown with a half angle of 30°. However, a single chamfer arrangement may be preferred, because of the lack of an edge which could cause wear as discussed below.

Preferably, the flared opening of the light guide interface portion has a very smooth surface. This is to avoid wear of the light guide on contact with the surface. Such wear could damage the light guide cladding, resulting in debris which blocks light transmission.

Smoothness may be measured as Roughness Average. Preferably, the flared opening has a surface of Roughness Average 16 to 32 microinch over a 0.004 inch long roughness cut-off (0.8 to 1.6 μm over a distance of 100 μm).

The flared opening of the light guide interface portion may be built to a particular smoothness specification or polished to achieve this, as discussed below.

The assay interrogating system of the reader has optical components including a lens, as discussed above.

Accurate positioning and angling of the lens are important in ensuring that the relative positioning of the light guide and lens is within the desired tolerance ranges set out above.

The lens is preferably mounted to the light guide interface portion of the reader. Suitably the light guide interface portion includes a recess in which the lens is positioned such that it can be optically coupled to the light guide. Suitably the recess comprises a retaining lip or other similar arrangement to control the position of the face of the lens adjacent to the optical sensor.

The lens is preferably held in place within the light guide interface portion using a lens-retaining insert.

In alternative arrangements, however, the lens and/or lens-retaining insert may be mounted directly to the reader housing, or to the optical system housing, e.g. by means of adhesive or a set screw, or the lens may be integrally formed with one of these components.

The lens-retaining insert may be held in position by a screw thread arrangement (preferably with at least a count of 3 to 4), by a press fit/interference fit arrangement (e.g. using crushed ribs), by a resilient arrangement (e.g. using a spring) and/or using adhesive. A combination of a screw thread arrangement and adhesive is envisaged. The lens-retaining insert must not interfere with the optical signal. The adhesive should transmit light in the near IR and visible regions, and should not fluoresce, particularly in those regions.

Preferably, the internal surfaces of the light guide interface portion and/or the optical system housing or reader housing in which the lens is mounted are optically black so as to reduce surface reflections (from signal or stray light) from reaching the light detectors. Suitably, these surfaces absorb wavelengths in the visible range (e.g. 300-800 nm). This may be achieved using coatings, e.g. having surface color and/or associated fine texture. The use of such coatings is particularly important if reflective metals are used in forming the device. Preferably, the internal surfaces are black in color. Black sealing tape may be used.

Suitable materials for the light guide interface portion include metals, plastics and ceramics. In a preferred embodiment the material used is steel e.g. stainless steel. Alternative materials include aluminum, titanium, KOVAR™, INVAR™ and other alloys used in optical applications, plastics such as polyoxymethylene (POM, DELRIN™), PVC, cyclic olefinic copolymers (COP/COC, TOPAS™, ZEONEX™, ZEONOR™ etc.). KOVAR™ and INVAR™ are preferred choices because of their low coefficients of thermal expansion.

Preferred plastics are optically black as discussed above. Metals can be oxidized (e.g. aluminum to aluminum hard or soft oxide coating, steel to black oxide and so on) or may have black material deposited or impregnated on the surface to absorb light in the visible or near IR range.

The lens-retaining insert is formed of steel or stainless steel in preferred embodiments. The materials used for the light guide interface portion and lens-retaining insert should ideally be of the same type to match coefficients of thermal expansion.

Further Components of Reader

The reader is preferably capable of reading, filtering, processing and/or transmitting optical signal values representing analyte concentration values. Preferably, the reader includes instrumentation to convert an optical signal from the optical sensor to an analyte concentration value. The reader may further comprise a transmitter for transmitting detected or measured analyte data.

Formation of Components

As explained above, the dimensions of the components, in particular the interface portion and the lens-retaining insert must be tightly controlled, and a smooth surface on the interface portion is desirable.

These components are preferably formed by molding or machining.

Multi-axis machining methods are appropriate to provide the desired tightly controlled dimensional tolerances. Swiss screw turning/machining is the preferred method. Deterministic machining and laser machining may be used.

For molded parts micro-molding is the preferred method. Preferably, the molding tools are precisely machined tools formed using multi-axis machining methods.

Preferably, the reader components are cleaned e.g. to remove particulates, debris, dirt, machine oils and/or low surface tension agents. Suitable solvents for cleaning include IPA, hexane, acetone and THF.

As mentioned above, the flared opening of the light guide interface portion may be built to a particular smoothness specification or polished to achieve this. It is important to use polishing materials which cannot impregnate the light guide interface portion and thereby abrade the light guide. For this reason, diamond polishing is not preferred. Hard wood is a preferred polishing material.

Implantation of Sensor

The distal portion of the sensor is preferably introduced subcutaneously or within the skin of a user e.g. into the dermis or epidermis. Alternatively it may be implanted in and/or through inter-peritoneal or peritoneal tissue. The user is preferably a human.

Preferably, the distal portion of the sensor is implanted or injected e.g. using a needle which may at least initially form part of the optical sensor as mentioned above. Preferably, the needle does not remain in the skin.

Systems Including Device

Optionally, the device also includes one or more non-optical sensors for the carbohydrate analyte e.g. electrochemical sensors as mentioned above. The electrochemical sensor may include a plurality of electrodes. Respective distal portions of the optical sensor and the non-optical sensor may be co-located within the user's body, and may be implanted together.

The device may form part of a system further comprising a hand-held monitor having a display and/or an insulin pump. The system may be a closed-loop system, with predictive diagnostics and minimal requirements for external calibration. The reader may wirelessly transmit analyte values to the hand-held monitor and/or insulin pump.

FURTHER ASPECTS OF INVENTION

In a second aspect, the invention relates to a reader for use in a device as described above, comprising an assay interrogating system including a lens; and a light guide interface portion comprising a flared opening adapted to receive a proximal portion of a light guide.

In a third aspect, the invention relates to a reader for use in a device as described above, comprising a housing; an assay interrogating system including a lens, and a lens-retaining insert holding the lens in position within the housing.

In a fourth aspect, the invention relates to a method of detecting or measuring a carbohydrate analyte using a device as described above, comprising detecting or measuring the optical signal readout of the assay components via the light guide using the assay interrogating system of the reader. The method may further comprise initial implantation of the assay components and distal portion of the light guide into the body of a user.

Preferably, and suitably between implantation and detection or measurement, the method further comprises a step of optically coupling the proximal portion of the light guide to the lens of the assay interrogating system via the interface portion. Preferably, the optical sensor and the reader are also connected via the connection arrangement.

The method may also include a step of separating the optical sensor and reader such that the proximal portion of the light guide and the lens of the assay interrogating system are no longer coupled. Optionally, the optical sensor is then replaced with a further optical sensor.

In a fifth aspect, the invention relates to an interface portion as described above.

All features described in connection with any aspect of the invention can be used with any other aspect of the invention.

DRAWINGS

The invention will be further described with reference to a preferred embodiment, as shown in the drawings in which.

DETAILED DESCRIPTION

Figure 1:
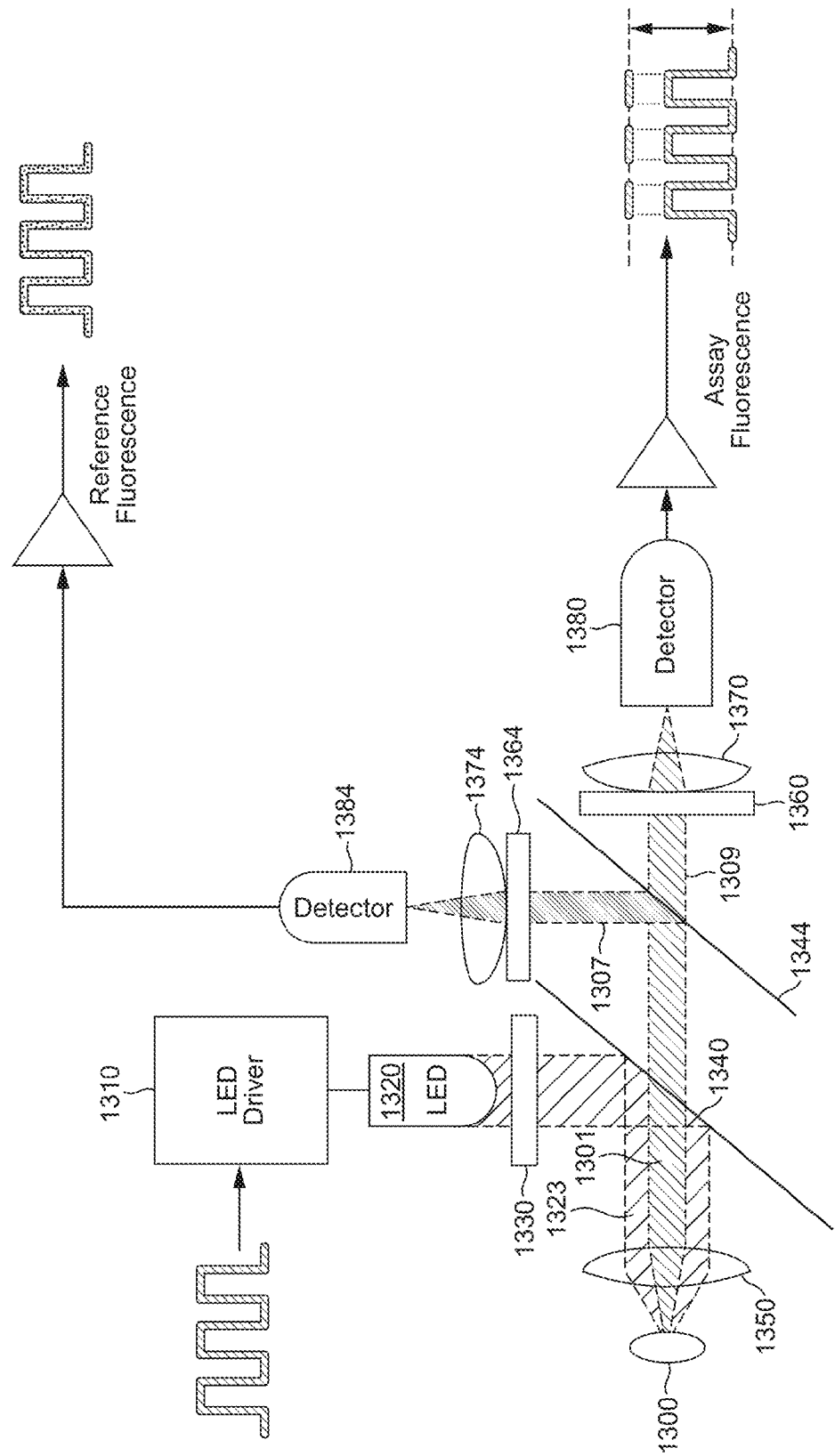
FIG. 1 shows schematically a preferred embodiment of the device of the invention, including the assay interrogating system.

In the following description, reference is made to the accompanying drawings which form a part hereof and which illustrate several embodiments of the present invention. It is understood that other embodiments may be utilized and structural and operational changes may be made without departing from the scope of the present invention.

Definitions

The term "optical axis" in relation to a lens refers to an imaginary line that defines the path along which light propagates through the system. Often but not necessarily this coincides with the mechanical axis and axis of rotational symmetry of the lens. The lens optical axis is shown as 14 in FIG. 7.

The term "optical axis" in relation to a light guide refers to an imaginary line that defines the path along which light propagates through the system. Often but not necessarily this coincides with the longitudinal axis and axis of rotational symmetry of the light guide. Where the light guide is not straight, the optical axis may be defined in terms of a cross-section. If the cross-section is cut such that the shape of the section is the same as the shape of the proximal end, typically the optical axis is a line that travels perpendicular to the cross-sectional face and through its centroid. The light guide optical axis is shown as 16 in FIG. 7.

The term "focal point" in relation to a lens refers to a point on the lens optical axis at which initially collimated rays are brought to a focus, e.g. in air; it is separated from the lens by the focal distance. A lens will typically have front and rear focal points. The focal point referred to herein is generally that on the same side as the light guide. The focal point is shown as 10 in FIG. 7.

The term "focal plane" in relation to a lens refers to a plane perpendicular to the lens optical axis and containing the focal point. This may also be referred to as the "back (or rear) focal plane". The focal plane is shown as 12 in FIG. 7.

The term "focal plane tolerance" (or transverse tolerance) as used herein refers to the range of positions of the light guide optical axis within the focal plane wherein coupling between the light guide and lens is such that light transmission is at least 80% of the maximum light transmission which occurs when the light guide optical axis is at the focal point of the lens.

The term "optical axis tolerance" (or axial tolerance) as used herein refers to the range of positions of the proximal end of the light guide along the lens optical axis wherein coupling between the light guide and lens is such that light transmission is at least 80% of the maximum light transmission which occurs when the proximal end of the light guide is at the focal point of the lens.

In the discussion herein, preferred embodiments of the devices, systems, and methods of the invention are described with reference to glucose as the analyte whose level/concentration in the blood and/or bodily fluids of the user is to be determined. However, this is by way of illustration and not limitation, as the principles, devices, systems, and methods of the present invention may be used for sensing and/or determining the level of a variety of other physiological parameters, agents, characteristics, and/or compositions.

The preferred embodiment of the device is shown schematically in FIG. 1. The device includes an optical sensor 100, shown in more detail in the following figures.

Optical Sensor of Preferred Embodiment

The optical sensor 100 includes a base 130 (FIGS. 4, 8) and an optical fiber 110 (also referred to herein as a "light guide") having a proximal portion 116 (FIG. 2) mounted to the base 130 as explained in more detail below.

The optical fiber 110 is formed of plastics having tensile and fatigue properties that ensure robustness.

Figure 2:
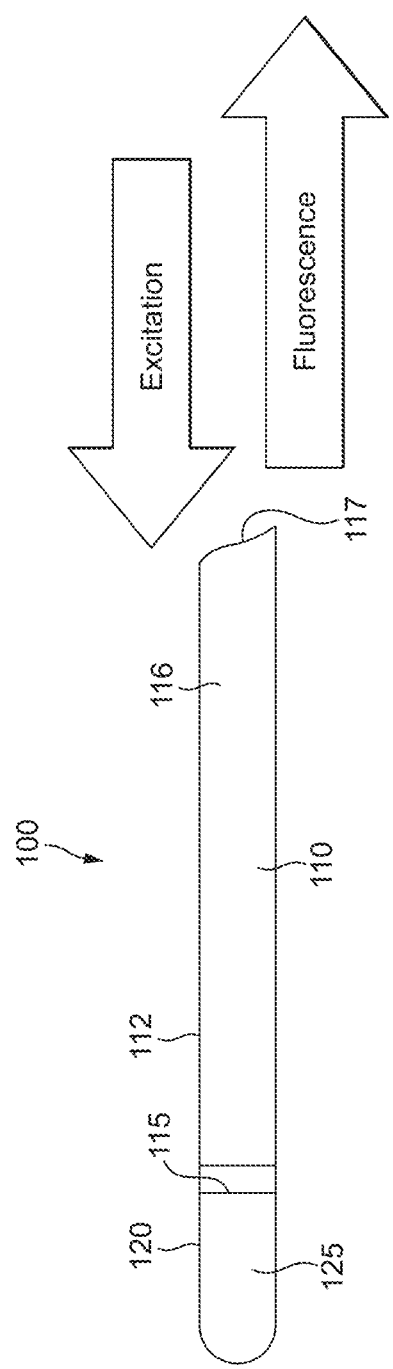
FIG. 2 shows the distal portion of the light guide of the optical sensor of FIG. 1 in more detail.
Figure 7:
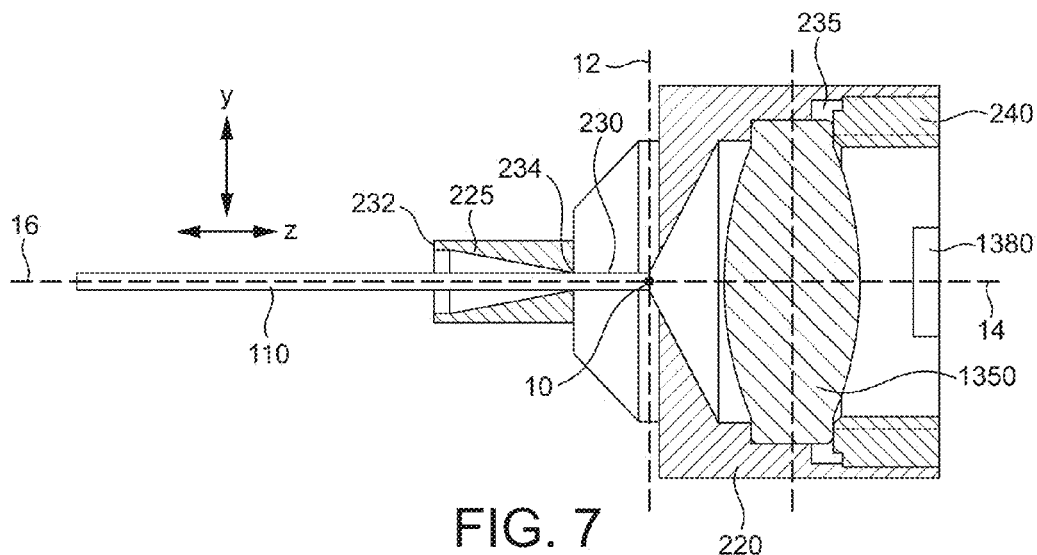
FIG. 7 is a cross-sectional view of the lens fiber interface portion of FIG. 6, also showing the proximal portion of the optical fiber, the lens and the lens-retaining insert.

The proximal portion 116 of the optical fiber 110 terminates in a proximal end 117 (in the form of a planar face perpendicular to the mechanical/optical axis 16 of the optical fiber 110 (FIGS. 2, 7).

The distal portion 112 of the optical fiber 110 (FIG. 2) is designed for insertion into a user's body as described in more detail below. A glucose-permeable membrane of PolyActive™ (a biocompatible, biodegradable polymer 1000PEGT70PBT30 from Integra Orthobiologics, Irvine, Calif.) is heat sealed to the fiber's distal end 115 to form an assay compartment 120 housing assay components 125.

Figure 5:
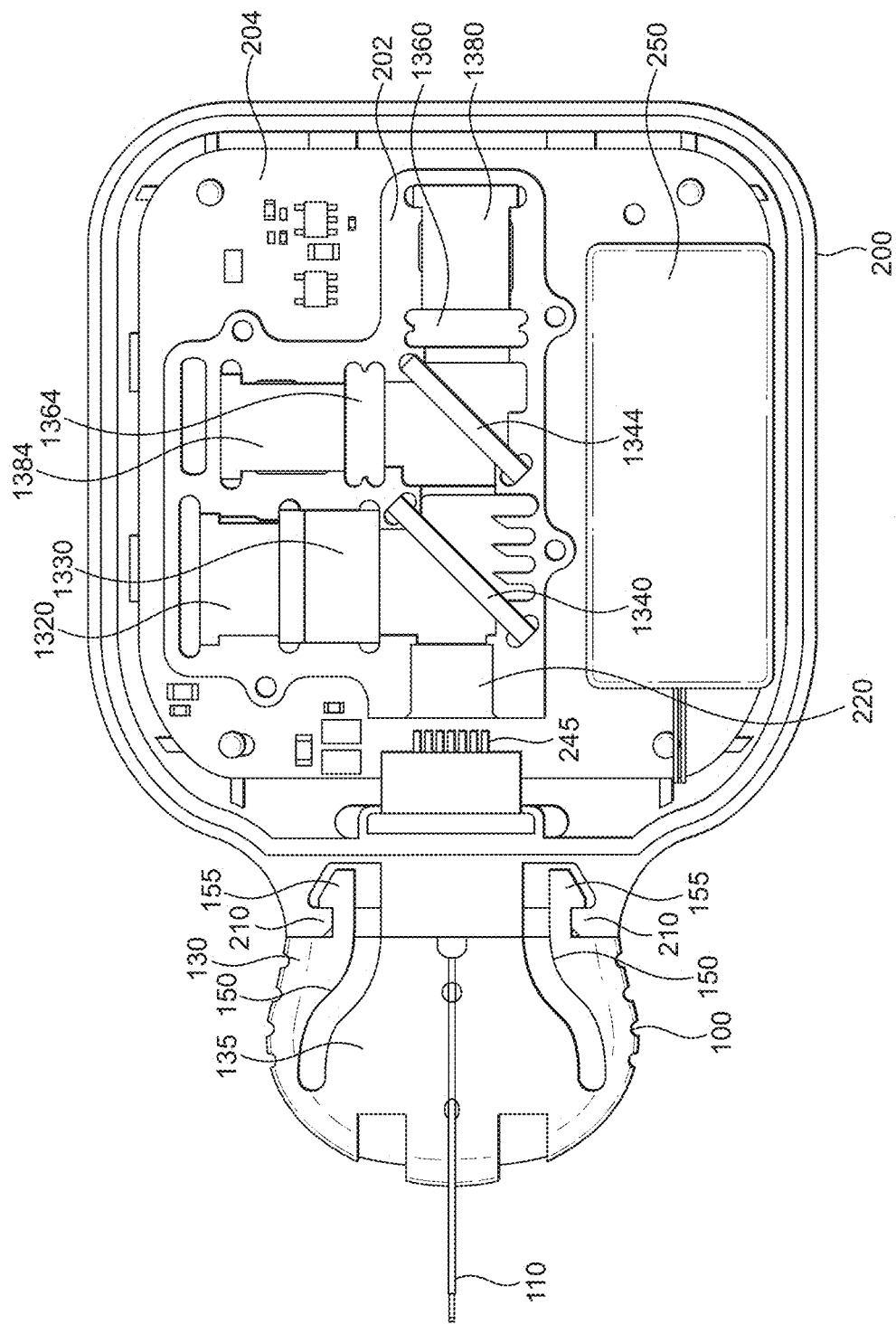
FIG. 5 is a plan view of the connected optical sensor and reader of FIG. 3b, with the upper shell of the reader housing removed.

The optical sensor base 130 is of polycarbonate. It is generally wide and flat in form, with a planar lower plate 135 (FIG. 5). The lower plate 135 is provided on its lower surface with a contact adhesive sheet (not shown) for mounting to a user's skin, the adhesive being initially protected by a cover sheet (not shown). The adhesive is capable of strong adhesion for 7 days.

Figure 4:
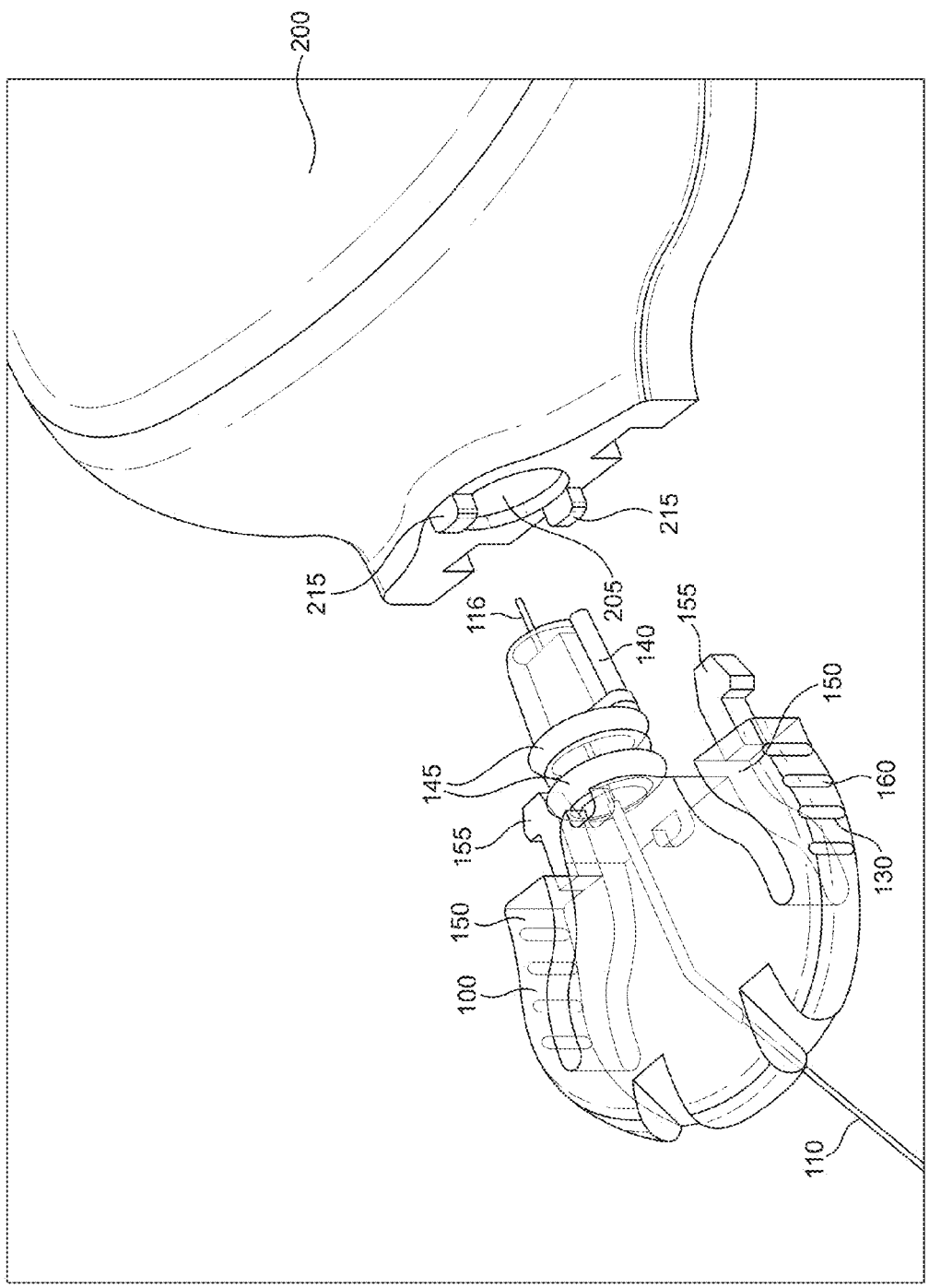
FIG. 4 is a perspective view of the optical sensor (left) and reader (right) of FIG. 3b before connection.
Figure 6:
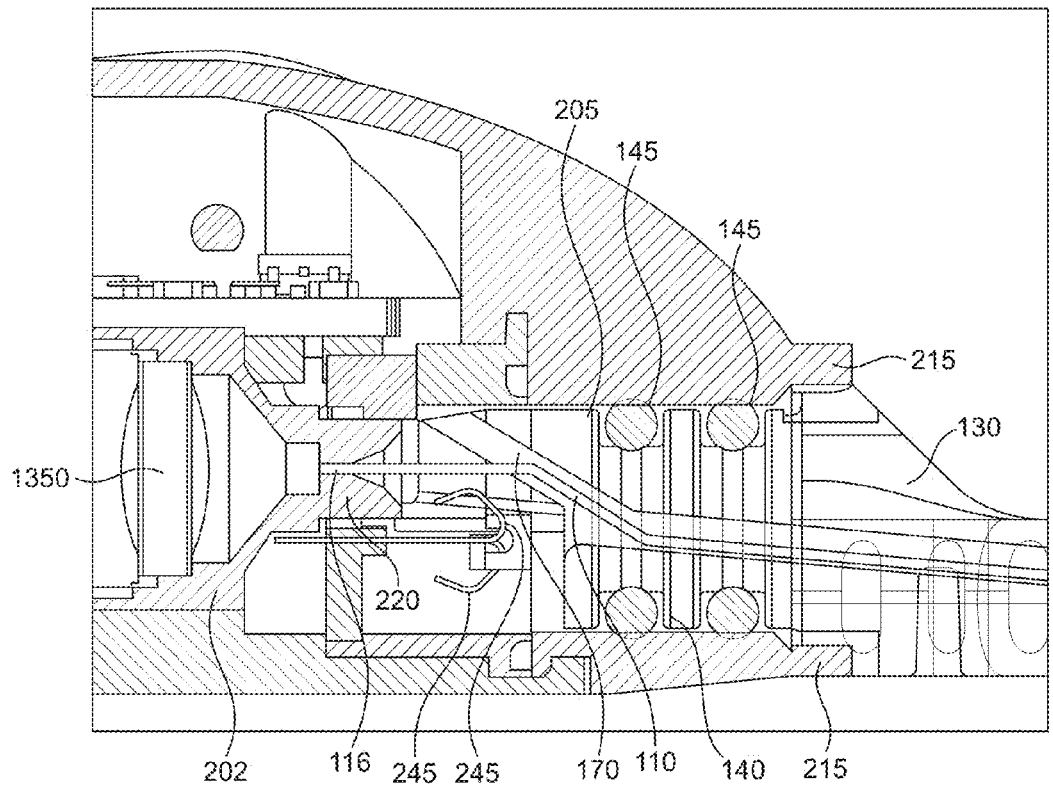
FIG. 6 is a cross-sectional view of the connection between the optical sensor and reader of FIG. 5.

The base has a front end for connection to the reader 200 as described in more detail below, and a back end (FIG. 4). A projecting portion 140 for insertion into the reader 200 extends from the front end of the optical sensor base 130 parallel to the lower plate 135; the projecting portion 140 is generally cylindrical in shape. The projecting portion 140 has two annular recesses, each being provided with an O-ring 145 (FIGS. 4, 6, 8).

Figure 8:
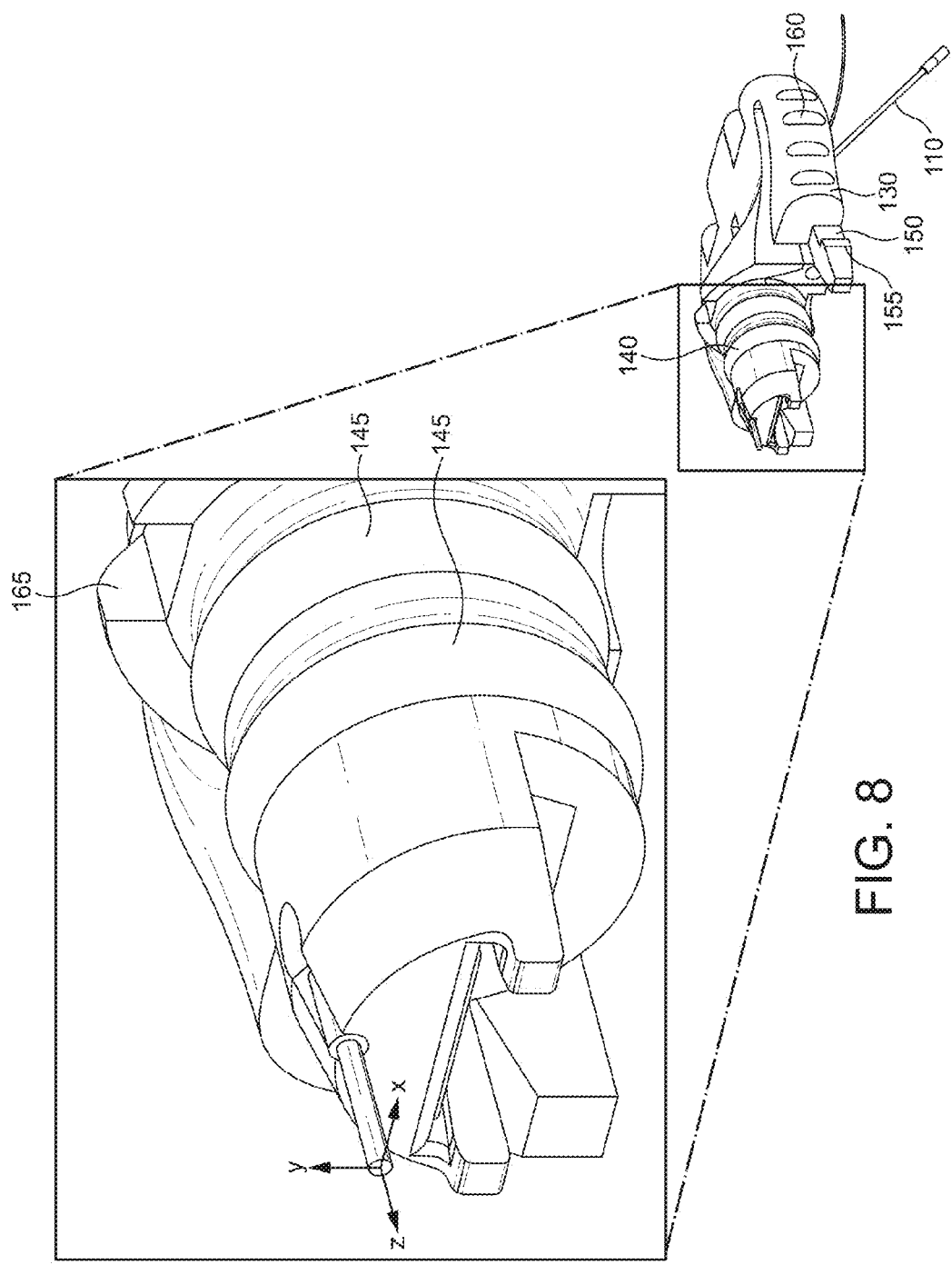
FIG. 8 is a perspective view of the optical sensor of FIG. 4, showing an enlarged view of the projecting portion.

A connector in the form of a resiliently biased flexible arm 150 extends along each side of the optical sensor base 130 from its back end to beyond its front end, separated from the body of the optical sensor base 150 by a space (FIGS. 4, 5, 8). The front end of each arm 150 terminates in a latch 155, such that there is a latch 155 on either side of the projecting portion 140. The arms 150 can be flexed inwards towards the projecting portion 140 but will return to their initial positions when released. Grips 160 in the form of ribs are provided on the outer sides of the arms to assist in flexing.

Above and below the projecting portion 140 of the optical sensor base 130, the optical sensor base 130 contains recesses 165 (FIG. 8) which form part of an anti-rotation arrangement as described below.

The optical sensor base 130 contains a through channel 170 (FIG. 6) extending from the back end to the projecting portion 140. The optical fiber 110 passes through the channel 170 and its proximal end 117 protrudes from a front face of the projecting portion 140 (FIGS. 4, 8). The optical fiber 110 is held in place within the optical sensor base 130 by UV-curing adhesive which is back-filled through the channel 170. The proximal end 117 of the optical fiber 110 is initially covered by a protective cap of vinyl plastics (not shown) which is held in place by the O-rings 145.

Figure 3A:
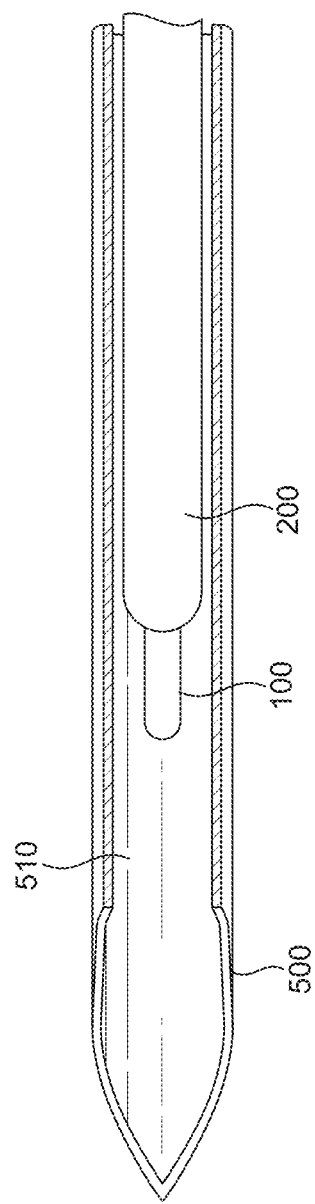
FIG. 3a is a side view of a needle for housing and deploying the distal portion of the light guide of the optical sensor of FIG. 2.
Figure 3B:
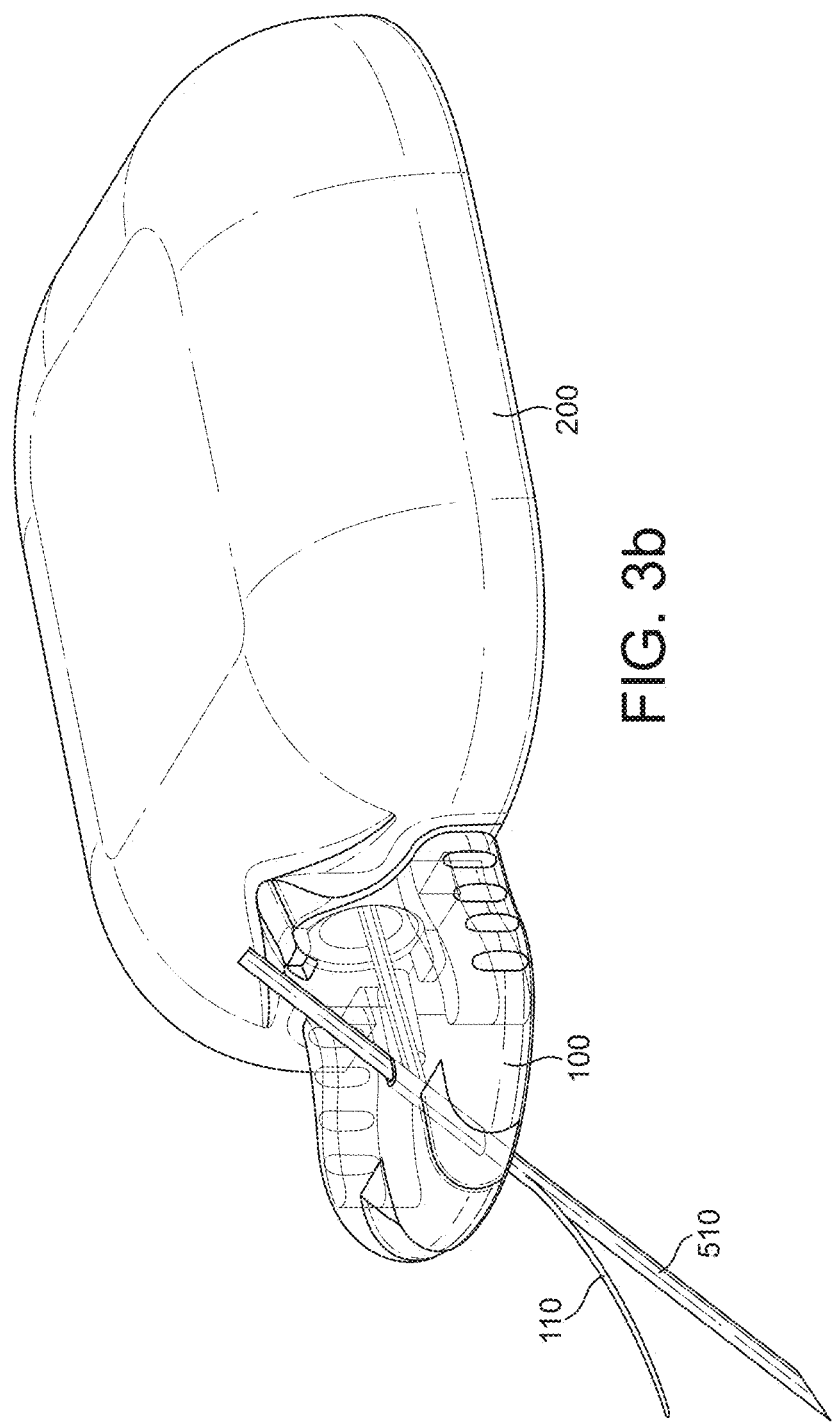
FIG. 3b is a perspective view of the connected optical sensor (left) and reader (right) of the preferred embodiment of the invention, showing the position of the needle of FIG. 3a before injection.

An insertion device 500 passes through a channel in the optical sensor base 130 at an angle of approximately 45° to the lower plate 135 (FIGS. 3a and 3b). The insertion device 500 relies on a disposable, automatically retracting needle 510 of C-shaped cross-section which is designed with the optical sensor base 130 to deliver the distal portion 112 of the optical sensor 100 through the user's skin at an angle of approximately 45°.

Reader of Preferred Embodiment

The reader 200 (FIGS. 4, 5, 6, 9) comprises a two-part housing of polycarbonate/acrylonitrile butadiene styrene blend (BAYBLEND™) having a base and an upper shell. The lower surface of the reader base is provided with one element of hook and loop fastening (not shown).

The reader 200 houses the optical system used to interrogate the assay (also referred to herein as the "assay interrogating system").

The optical system (FIGS. 1, 5) is essentially a modified epi-fluorescence set-up with one light source to excite (i.e. illuminate) the assay and two detectors to detect the fluorescence emitted from the assay and the internal reference, respectively. As noted, the intensity of the emitted fluorescence correlates to the glucose concentration. Here, the measured intensity of the emitted fluorescence is affected by the intensity of the light source and the coupling between the assay and the optical system.

A driver circuit 1310 modulates a LED 1320 at a low frequency (solely with the purpose of eliminating the 1/f noise and canceling out ambient light) with a wavelength range capable of simultaneously exciting the assay and reference fluorophores. The LED output is filtered using a multilayer dielectrical filter 1330 to select a distinct wavelength region. The filtered LED output is reflected by a first dichroic beam splitter 1340 and focused onto the optical sensor 1300/100, which includes the assay and the reference (also referred to herein as the "reference fluorophore"), by a lens 1350. The interface between the optical sensor and the lens 1350 is described in more detail below.

The assay and the reference emit fluorescence. The emitted fluorescence 1301 and the reflected excitation light 1323 are picked up and collimated by the lens 1350. The first dichroic beam splitter 1340 transmits the fluorescence 1301. However, it reflects the majority of the back reflected excitation light 1323. A second beam splitter 1344 reflects the reference fluorescence 1307 at a 90° angle, but it transmits the assay fluorescence 1309. A first emission filter 1360 with a distinct wavelength region red shifted with respect to, and not overlapping, the pass band of the excitation filter and matching the desired part of the assay fluorescence spectrum then blocks the remaining part of the excitation light and transmits the assay fluorescence. Similarly, a second emission filter 1364 with a distinct wavelength region red shifted with respect to, and not overlapping, the pass band of the excitation filter and matching the desired part of the assay fluorescence blocks the remaining part of the excitation light and transmits the reference fluorescence 1307. Thus, in effect, only the fluorescence from the assay and the fluorescence from the reference are focused onto their respective photo detectors (also referred to herein as "light detectors") 1380, 1384 using respective lenses 1370, 1374. The ratio between the detected assay fluorescence and the detected reference fluorescence correlates with the glucose concentration in the assay.

The optical system is mounted within the reader housing in an optically black optical system housing 202 (FIG. 5). Components of the optical system are electrically connected to a printed circuit board assembly 204.

The light guide interface portion 220 of the reader 200 is now described.

Figure 9:
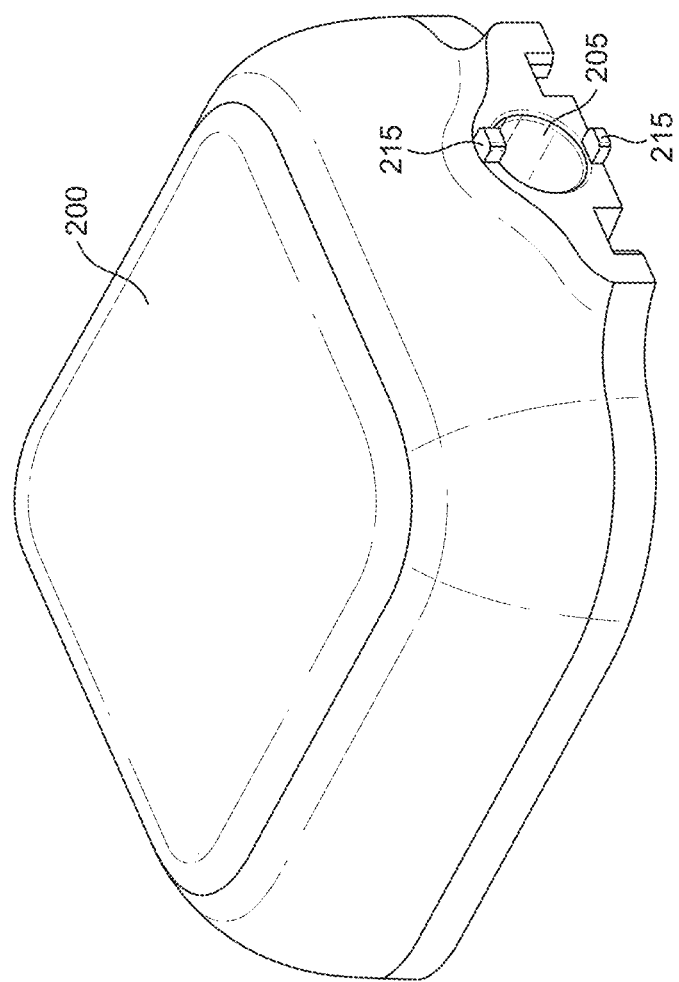
FIG. 9 is a perspective view of the reader of FIG. 4.
Figure 10:
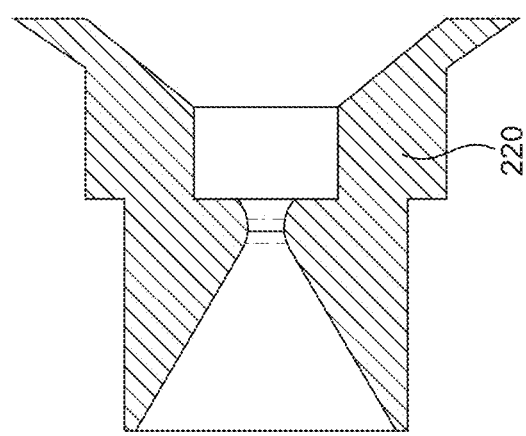
FIG. 10 is a cross-sectional view of two lens fiber interface portions alternative to that of FIG. 7.
Figure 10:
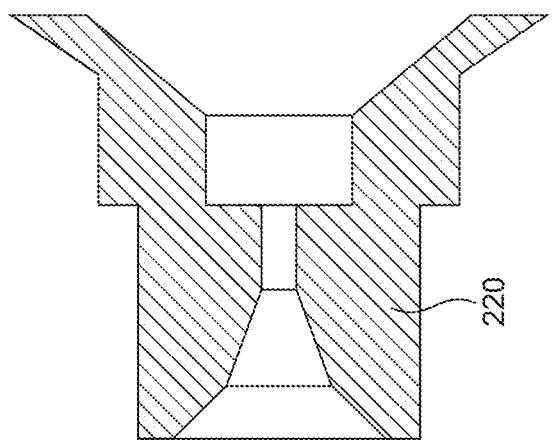

The reader housing includes a generally cylindrical bore 205 into which the projecting portion 140 of the optical sensor base 130 is to be inserted (FIGS. 6, 9). The inside surface of the bore 205 engages the O-rings 145 of the optical sensor base 130 (FIG. 6). Two fixed connectors in the form of projections 210 complementary to the latches 155 on the optical sensor base 130 are located at the mouth of the reader housing bore 205 (FIG. 5). Above and below the bore 205, the reader housing is provided with lugs 215 as part of the anti-rotation arrangement (FIG. 9).

The light guide interface portion 220 of the reader 200 is mounted within the optical system housing 202 at the internal end of the reader housing bore (FIGS. 5, 6). This light guide interface portion 220 is shown in FIG. 7.

The light guide interface portion 220 is generally in the form of a stepped cylindrical block having a through channel as described below. The block is formed by machining. At the inner end of the block as defined below, the block wall is notched such that it forms three fingers (not shown).

From the outer end to the inner end (i.e. moving away from the optical sensor 100 when connected to the reader 200 in use) the channel has a smooth flared opening in the form of a frustoconical portion 225 of half angle 30° with a wide mouth 232; a narrow light guide alignment channel 230 of constant diameter extending from the narrow end 234 of the frustoconical part 230, and a wide recess 235 in which the lens 1350 is mounted, the wide recess 235 being defined by the three fingers of the block wall, which are provided with an internal screw thread.

The lens 1350 is a biconvex convergent lens of focal length approximately 2 mm. The lens 1350 is mounted with its optical axis 14 parallel to and aligned with the light guide alignment channel 230. The lens 1350 is held in place by a generally tubular lens-retaining insert 240 of complementary shape to the lens 1350. The lens-retaining insert 240 has an external screw thread which engages the internal screw thread of the light guide interface portion 220. The lens-retaining insert 240 is also fixed in position by means of adhesive. The assay photodetector 1380 is positioned within the lens-retaining insert 240 such that light is focused onto it by the lens 1350.

The reader 200 houses further components (not all shown) including diagnostics, one or more microprocessors and/or digital signal processors (DSPs), memory, a RF communication chip (using, e.g., 2.4 GHz TelD protocol), and a rechargeable battery 250. The reader is capable of the conversion of signals received from the sensors to glucose values and of wireless communication, including transmission of the glucose values (or an averaged, weighted, or otherwise modified version thereof) to a monitor, an infusion pump or a display device (not shown).

The reader includes electrical contacts 245 for interface with a charger (not shown) and with the optical sensor base 130.

Use of Device

In use, the optical sensor base 130 is mounted to the skin of a user by removal of the cover sheet and application of the adhesive to the skin. The distal portion 112 of the optical fiber 110 of the optical sensor 100, including the assay compartment 120, is implanted subcutaneously using insertion device 500. The needle 510 automatically retracts. The optical sensor base 130 is further secured to the skin by overtaping (not shown) to reduce the risk of the optical sensor 100 being pulled out of the skin accidentally. The overtaping has an element of hook and loop fastening (not shown) complementary to that on the reader base.

The reader 200 is connected to the optical sensor 100 as follows.

The projecting portion 140 of the optical sensor base 130 is pushed into the bore 205 of the reader 200. The positional tolerance of the projecting portion 140 within the bore 205 is approximately ±0.02 inches (±500 μm) in the x and y directions. This locates the proximal end 117 of the optical fiber 115 within the frustoconical portion 225 of the light guide interface portion 220 of the reader 200.

The frustoconical portion 225 serves to direct the proximal end 117 of the optical fiber 115 into the light guide alignment channel 230 so that it is constrained in the x and y directions. The positional tolerance of the optical fiber 115 inside the light guide alignment channel 230 is approximately ±10 μm.

The arms 150 of the optical sensor base 130 are flexed inwards using the grips 160. When the optical sensor projecting portion 140 is fully inserted into the reader 200, the arms 150 are released and return to their initial positions, wherein the latches 155 engage the projections 210 of the reader 200 such that the optical sensor 100 and reader 200 cannot be separated by pulling apart. The O-rings 145 of the optical sensor 100 engage the bore 205 of the reader 200 to prevent relative movement of the optical fiber 110 and the lens 1350 of the reader in the z direction. The O-rings 145 provide a radial seal between the optical sensor 100 and the reader 200 to water-resistance standard IPX8.

When the optical sensor 100 and reader 200 are connected, lugs 215 of the reader 200 engage recesses 165 of the optical sensor 100 in an anti-rotation arrangement, preventing relative rotation of the optical sensor 100 and reader 200.

Thus, the proximal end 117 of the optical fiber 110 is constrained at or very close to the focal point 10 of the lens 1350, with the lens optical axis 14 and optical fiber optical axis 16 aligned.

Relative motion between the reader 200 and sensor 100 is further prevented by engagement of the complementary hook and loop fastening elements of the reader base and the sensor overtaping.

The assay interrogating system is interrogated as explained above. As shown in FIG. 2, excitation light travels from the proximal end 117 of the optical fiber 115 to the assay components 125, and the fluorescence response travels back up the optical fiber 110 to the assay interrogating system. Light from the proximal end 117 of the optical fiber 115 is focused by the lens 1350 onto the light detector 1380. Accurate relative positioning of the proximal end 117 of the optical fiber 110 and the lens 1350 ensures that light is efficiently coupled from the optical fiber 110 into the assay interrogating system.

To separate the optical sensor 100 from the reader 200, the optical sensor connector arms 150 are flexed inwards to release the latches 155 from the reader connector projections 210, after which the reader 200 slides easily away from the optical sensor 100.

Figure 11:
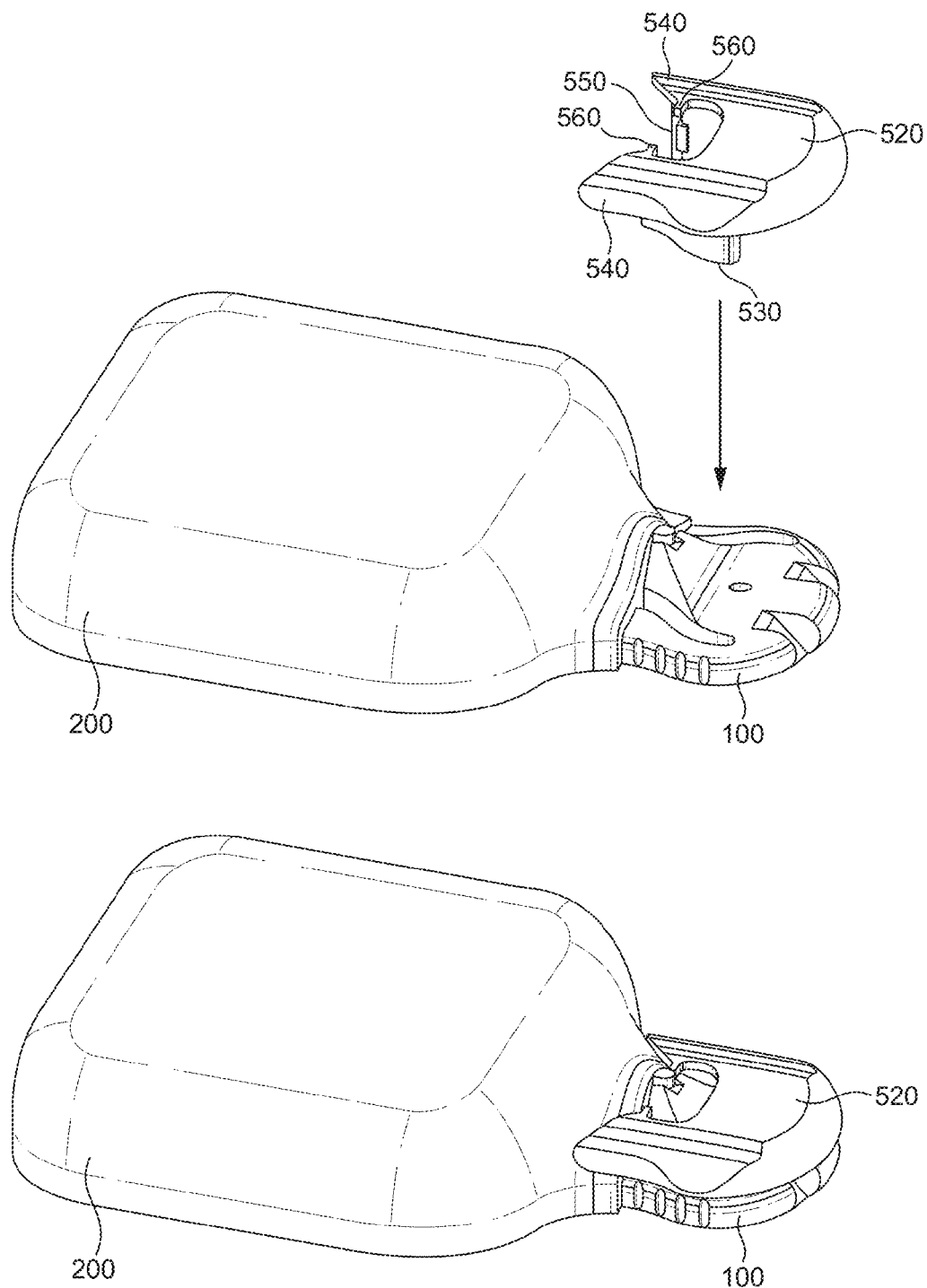
FIG. 11 is a perspective view of an alternative embodiment of the invention, including a locking component. The locking component is shown before and after engagement with the sensor and reader (top and bottom respectively).

In an alternative embodiment shown in FIG. 11, a further separate locking component 520 is provided to inhibit relative motion between the reader 200 and optical sensor 100. The locking component 520 is of plastics, and is adapted to engage the upper surface of the optical sensor base 130 and adjacent parts of the shell of the reader 200 when the optical sensor 100 and reader 200 are connected. Thus, the locking component 520 is generally in the form of a plate complementary to the upper surface of the optical sensor base 130, but with a space 550 at the forward central part. Descending parts 530 of the locking component 520 correspond to the spaces between the sensor body and the flexible arms 150. Forward wings 540 of the locking component 520 are complementary to the upper surface of adjacent parts of the shell of the reader 200. A tab 560 extends from each wing 540 into the space 550.

The locking component 520 is connected to and disconnected from the connected optical sensor 100 and reader 200 vertically (i.e. in the y direction). The locking component 520 lies generally above the optical sensor base 130, with forward wings 540 engaging the shell of the reader 200. Parts 530 engage the spaces defined by the optical sensor base 130, flexible arms 150 and reader body, preventing the optical sensor base 130 from moving further towards the reader 200. Tabs 560 occupy positions between the optical sensor 100 and reader 200 to either side of the lugs 215/ recesses 165 of the anti-rotation arrangement described above, preventing the optical sensor base 130 from moving away from the reader 200. In this way, the locking component 520 prevents relative movement between the optical sensor 100 and reader 200, especially in the z direction.

EXAMPLES

Comparative Example

In an optical sensor with the optical fiber optical axis parallel to the lens optical axis, it was found that if the optical fiber optical axis was not within ±50 μm of the lens optical axis in the x and y directions, the optical signal was reduced by 20 to 50%. Theory suggests that if the optical fiber optical axis was not within ±100 μm of the lens optical axis, the optical signal would be reduced by 80%.

It was also found that if the proximal end of the optical fiber was not within ±200 µm of the lens focal point in the z direction, the optical signal was reduced by 20% (experimental results) to 30% (theoretical results). The relationship between distance and performance was not linear, and performance dropped off at an increasing rate as the proximal end of the optical fiber was moved away from the focal point.

Advantages of the preferred embodiments of the invention include:

- the tolerance in the x and y directions permitted by the light guide alignment channel of the light guide interface portion of the reader is very low, whereas the tolerance in the z direction permitted by the connection between the reader and the optical sensor is slightly higher. It was a contribution of the present inventors to realize that higher tolerance in the z direction is acceptable. It was a further contribution of the present inventors to appreciate that different arrangements can be used to constrain movement in the x and y directions and the z direction.
- The smooth flared opening of the light guide interface portion assists in insertion of the optical fiber into the very narrow light guide alignment channel. Without this feature it would be difficult to insert the delicate optical fiber into the light guide channel without damaging the optical fiber.
- The light guide interface portion is included on the reader rather than the optical sensor. The reader has a longer life than the optical sensor, and so this type of arrangement is more cost-effective.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, and all changes which come within the meaning and range of equivalency of the claims are therefore intended to be embraced therein.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than to mean 'consisting of'. All prior teachings acknowledged above are hereby incorporated by reference. No acknowledgement of any prior published document herein should be taken to be an admission or representation that the teaching thereof was common general knowledge at the date hereof.

The invention claimed is:

1. A device for the detection or measurement of a carbohydrate analyte in fluid comprising:
   an optical sensor comprising components of an assay for carbohydrate analyte, the readout of which is a detectable or measurable optical signal, and a light guide having a distal end optically coupled to the assay components and a proximal end; and
   a reader for interrogating the optical sensor, the reader comprising an assay interrogating system including a lens; and
   an interface comprising a flared opening adapted to receive the proximal end of the light guide, the interface forming part of at least one of the optical sensor and the reader, the interface including a first portion configured for removably constraining the proximal end of the light guide and a second portion configured for removably constraining the lens of the assay interrogating system in an optically coupled axial arrangement with the light guide; wherein the flared opening of the interface terminates in a channel adapted to accommodate the proximal end of the light guide.

2. A device as claimed in claim 1, wherein in use the proximal end of the light guide is disposed externally to a body of a user and the distal end of the light guide and the assay components are placed internally in the user's body.

3. A device as claimed in claim 1, wherein when the proximal end of the light guide and the lens are constrained in the optically coupled arrangement, the proximal end of the light guide is within the focal plane tolerance and optical axis tolerance of the lens.

4. A device as claimed in claim 1, wherein when the proximal end of the light guide and the lens are constrained in the optically coupled arrangement, an optical axis of the lens is parallel to an optical axis of the light guide as measured at the proximal end of the light guide.

5. A device as claimed in claim 1, wherein when the proximal end of the light guide and the lens are constrained in the optically coupled arrangement, the interface constrains the relative position of the light guide and lens in directions perpendicular to an optical axis of the lens.

6. A device as claimed in claim 1, wherein when the proximal end of the light guide and the lens are constrained in the optically coupled arrangement, the relative position of the light guide and lens is constrained within a tolerance range of less than or equal to ±50 µm in directions perpendicular to an optical axis of the lens.

7. A device as claimed in claim 1, further comprising a detachable connection between the optical sensor and the reader, the detachable connection being capable of further constraining the proximal end of the light guide and the lens of the assay interrogating system within the optically coupled arrangement.

8. A device as claimed in claim 7, wherein when the proximal end of the light guide and the lens are constrained in the optically coupled arrangement, the detachable connection constrains the relative position of the light guide and lens in directions parallel to an optical axis of the lens.

9. A device as claimed in claim 7, wherein the detachable connection between the optical sensor and the reader comprises a projecting portion of the optical sensor and a bore of the reader, the projecting portion being capable of engaging the bore.

10. A device as claimed in claim 7, wherein the detachable connection between the optical sensor and the reader comprises moveable fasteners on at least one of the optical sensor and the reader.

11. A device as claimed in claim 7, further comprising a locking component comprising a plate complementary to the upper surface of an optical sensor base, wherein the locking component is capable of inhibiting relative movement between the optical sensor and the reader.

12. A device as claimed in claim 7, further comprising an anti-rotation arrangement capable of inhibiting relative rotation of the optical sensor and reader in the optically coupled arrangement.

13. A device as claimed in claim 1, wherein when the proximal end of the light guide and the lens are constrained in the optically coupled arrangement, the relative position of the light guide and lens is constrained within a tolerance range of less than or equal to ±200 µm in a direction parallel to an optical axis of the lens.

14. A device as claimed in claim 13, wherein when the proximal end of the light guide and the lens are constrained in the optically coupled arrangement, the relative position of the light guide and lens is constrained within a tolerance range of less than or equal to ±100 µm in the direction parallel to the optical axis of the lens.

15. A device as claimed in claim 1, wherein the flared opening has a surface of Roughness Average 0.8 to 1.6 µm over a distance of 100 µm.

16. A device as claimed in claim 1, wherein the flared opening comprises a single chamber.

17. A device as claimed in claim 1, wherein the flared opening of the light guide interface of the reader is frusto-conical in shape.

18. A device as claimed in claim 1, wherein the lens is mounted to the light guide interface of the reader.

19. A device as claimed in claim 18, wherein the lens is held in place by a lens-retaining insert.

20. A device as claimed in claim 19, wherein the lens-retaining insert is held in position by one or more arrangements selected from the group consisting of a screw thread arrangement, a friction fit arrangement, a resilient arrangement and an adhesive arrangement.

21. A device as claimed in claim 1, wherein the light guide comprises one or more optical fibers.

22. A device as claimed in claim 1, wherein the light guide has at least one cross-sectional dimension in the range of 50 µm to 600 µm.

23. A device as claimed in claim 1, wherein the assay interrogating system is a stacked planar integrated optical system (SPIOS).

24. A device as claimed in claim 1, wherein the assay interrogating system includes an illumination source.

25. A device as claimed in claim 24, wherein said illumination source is a red laser diode.

26. A device as claimed in claim 1, wherein the components of the assay are retained in an assay compartment defined by the distal end of the light guide and a material that permits diffusion of the analyte but not the assay components.

27. A device as claimed in claim 1, wherein the components of the assay include an analyte binding molecule labelled with one of a proximity based signal generating/modulating moiety pair; and
an analyte analog capable of competing with the analyte for binding to the analyte binding molecule labelled with the other of the proximity based signal generating/modulating moiety pair.

28. A device as claimed in claim 27, wherein the analyte binding molecule comprises mannose binding lectin labelled with one of the proximity based signal generating/modulating moiety pair and the analyte analog comprises dextran labelled with the other of the proximity based signal generating/modulating moiety pair.

29. A device as claimed in claim 27, wherein one of the proximity based signal generating/modulating moiety pair is selected from Alexa Fluor 647 (AF647), Alexa Fluor 750 (AF750), and QSY 21.

30. A device as claimed in claim 27, wherein one of the proximity based signal generating/modulating moiety pair is hexamethoxy crystal violet-1 (HMCV-1).

31. A device as claimed in claim 27, wherein the assay components further comprise a reference fluorophore.

32. A device as claimed in claim 31, wherein said reference fluorophore is Alexa Fluor 700 (AF700).

33. A device as claimed in claim 1, wherein the analyte is glucose.

34. A device as claimed in claim 1, further comprising a non-optical analyte sensor.

35. A device as claimed in claim 34, wherein the non-optical analyte sensor is an electrochemical sensor.

36. A system comprising a device as claimed in claim 1 and a monitor displaying analyte data.

* * * * *